(12) United States Patent
Petersen et al.

(10) Patent No.: US 8,999,390 B2
(45) Date of Patent: *Apr. 7, 2015

(54) SUSTAINED RELEASE FORMULATION COMPRISING OCTREOTIDE AND THREE LINEAR POLYLACTIDE-CO-GLYCOLIDE POLYMERS

(75) Inventors: Holger Petersen, Eimeldingen (DE); Markus Ahlheim, Staufen (DE)

(73) Assignee: Novartis AG, Basel (CH)

( * ) Notice: Subject to any disclaimer, the term of this patent is extended or adjusted under 35 U.S.C. 154(b) by 201 days.

This patent is subject to a terminal disclaimer.

(21) Appl. No.: 13/472,219

(22) Filed: May 15, 2012

(65) Prior Publication Data

US 2012/0226224 A1 Sep. 6, 2012

Related U.S. Application Data

(63) Continuation of application No. 12/865,145, filed as application No. PCT/EP2009/051026 on Jan. 29, 2009.

(30) Foreign Application Priority Data

Jan. 30, 2008 (EP) ..................... 08150826

(51) Int. Cl.
| | |
|---|---|
| *A61K 9/14* | (2006.01) |
| *A61K 38/31* | (2006.01) |
| *A61K 9/16* | (2006.01) |
| *A61K 9/00* | (2006.01) |
| *A61K 9/06* | (2006.01) |
| *A61K 9/10* | (2006.01) |

(52) U.S. Cl.
CPC ............ *A61K 9/1694* (2013.01); *A61K 9/0019* (2013.01); *A61K 9/0024* (2013.01); *A61K 9/06* (2013.01); *A61K 9/10* (2013.01); *A61K 9/1647* (2013.01); *A61K 38/31* (2013.01)

(58) Field of Classification Search
None
See application file for complete search history.

(56) References Cited

U.S. PATENT DOCUMENTS

| | | | |
|---|---|---|---|
| 5,688,530 A | 11/1997 | Bodmer et al. | |
| 5,876,761 A * | 3/1999 | Bodmer et al. | ............... 424/501 |
| 6,217,893 B1 * | 4/2001 | Pellet et al. | ................... 424/426 |
| 2007/0092574 A1 | 4/2007 | Cook | |

FOREIGN PATENT DOCUMENTS

| | | |
|---|---|---|
| CA | 2316052 | 1/1991 |
| GB | 2265311 | 9/1993 |
| WO | WO 2004/011054 | 2/2004 |
| WO | WO 2004/043432 | 5/2004 |
| WO | WO 2004112752 A1 * | 12/2004 |
| WO | WO 2005/009357 | 2/2005 |
| WO | WO 2005/046645 | 5/2005 |
| WO | WO 2005046645 A1 * | 5/2005 |
| WO | WO 2007/071395 | 6/2007 |

OTHER PUBLICATIONS

Jain R.A., ,,The manufacturing techniques of various drug loaded biodegradable poly(lactide-*co*-glycolide) (PLGA) devices, Biomaterials, vol. 21, No. 23, pp. 2475-2490, 2000.

Lambert W.J. et al., "Development of an in situ forming biodegradable poly-lactide-co-glycolide system for the controlled release o proteins", Journal of Controlled Release, vol. 33, No. 1,1995, pp. 189-195.

Ravivarapu H.B. et al., "Polymer and microsphere blending to alter the release of a peptide from PJGA microspheres", European Journal of Pharmaceutics and Biopharmaceutics, vol. 50, No. 2, 2000, pp. 263-270.

* cited by examiner

*Primary Examiner* — H. Sarah Park
(74) *Attorney, Agent, or Firm* — Gregory Houghton; George R. Dohmann

(57) ABSTRACT

The present invention relates to sustained release formulations comprising as active ingredient octreotide or a pharmaceutically-acceptable salt thereof and three different linear polylactide-co-glycolide polymers (PLGAs).

11 Claims, No Drawings

SUSTAINED RELEASE FORMULATION COMPRISING OCTREOTIDE AND THREE LINEAR POLYLACTIDE-CO-GLYCOLIDE POLYMERS

This application is a continuation of U.S. Ser. No. 12/865,145 filed Jul. 29, 2010 which is a 371 of PCT/EP2009/051026 filed on Jan. 29, 2009, which claims benefit of EP application 08150826.9 filed on Jan. 30, 2008, which in their entirety are herein incorporated by reference.

The present invention relates to sustained release formulations comprising as active ingredient octreotide or a pharmaceutically-acceptable salt thereof and three different linear polylactide-co-glycolide polymers (PLGAs).

These pharmaceutical compositions according to the present invention are indicated for inter alia long-term maintenance therapy in acromegalic patients, and treatment of severe diarrhea and flushing associated with malignant carcinoid tumors and vasoactive intestinal peptide tumors (vipoma tumors).

Peptide drugs are usually administerd systemically, e.g. parenterally. However, parenteral administration may be painful and cause discomfort, especially for repeated daily administrations. In order to minimize the number of injections to a patient, the drug substance should be administered as a depot formulation. A common drawback with injectable depot formulations is the fluctuation in plasma levels such as high peak levels together with plasma levels close to zero during the entire release periode.

Sustained release formulations comprising as active ingredient octreotide or a pharmaceutically acceptable salt thereof and two or more different polylactide-co-glycolide polymers (PLGAs) have, for instance, been also disclosed in WO2007/071395.

The present invention discloses a sustained release formulation comprising as active ingredient (drug substance) octreotide or a pharmaceutically-acceptable salt thereof. Octreotide is a somatostatin analog having the following formula:

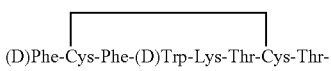
(D)Phe-Cys-Phe-(D)Trp-Lys-Thr-Cys-Thr-

The active ingredient may be in the form of a pharmaceutically acceptable salt of octreotide, such as an acid addition salt with e.g. inorganic acid, polymeric acid or organic acid, for example with hydrochloric acid, acetic acid, lactic acid, citric acid, fumaric acid, malonic acid, maleic acid, tartaric acid, aspartic acid, benzoic acid, succinic acid or pamoic (embonic) acid. Acid addition salts may exist as mono- or divalent salts, e.g. depending whether 1 or 2 acid equivalents are added. Preferred is the pamoate monosalt of octreotide.

The particle size distribution of the drug substance influences the release profile of the drug from the depot form. The drug substance which is used to prepare the depot formulation is crystalline or in the form of an amorphous powder. Preferred is an amorphous powder which has a particle of a size of about 0.1 microns to about 15 microns (99%>0.1 microns, 99%<15 microns), preferably from 1 to less than about 10 microns (90%>1 microns, 90%<10 microns). The drug substance preferentially undergoes a micronization process to present the required particle size distribution.

The present invention further provides a sustained release pharmaceutical composition (depot) comprising as active ingredient octreotide or a pharmaceutically-acceptable salt thereof incorporated in blends or mixtures of poly(lactide-co-glycolide)s (PLGAs), for instance in form of microparticles, implants or semisolid formulations.

Alternatively to blends of PLGAs, in another aspect of the present invention the pharmaceutical composition comprises a mixture of PLGA polymers containing the active ingredient; i.e. the active ingredient may be incorporated into one or more PLGAs in form of microparticles, implants or semisolid formulations and is then mixed with another microparticle or implant or semisolid formulation also comprising the active ingredient and one or more PLGAs.

The pharmaceutical composition according to the present invention allows a sustained release of the active ingredient over a period of more than three month, preferentially between three and six months. During the release of the active ingredient the plasma levels of octreotide are within the therapeutic range. It is understood that the exact dose of octreotide will depend on a number of factors, including the condition to be treated, the severity of the condition to be treated, the weight of the subject and the duration of therapy.

Surprisingly fluctuations in plasma levels can significantly be reduced by using a suitable combination of three different linear PLGAs in the pharmaceutical composition according to the present invention.

The drug substance is incorporated into a biodegradable polymer matrix consisting of three different linear polylactide-co-glycolide polymers (PLGAs). The PLGAs have a lactide:glycolide monomer ratio of 100:0 to 40:60, preferably 90:10 to 40:60, more preferably 85:15 to 65:35.

The PLGAs according to the present invention have a molecular weight (Mw) ranging from 1,000 to 500,000 Da, preferably from 5,000 to 100,000 Da. The architecture of the polymers is linear.

The inherent viscosity (IV) of the PLGAs according to the present invention is below 0.9 dl/g in $CHCl_3$, preferentially below 0.8 dl/g in $CHCl_3$. The inherent viscosities can be measured by the conventional methods of flow time measurement, as described for example in "Pharmacopoée Européenne", 1997, pages 17-18 (capillary tube method). Unless stated otherwise, these viscosities have been measured in chloroform at a concentration of 0.5% at 25° C. or in hexaisofluoropropanol at a concentration of 0.5% at 30° C.

End groups of the PLGAs according to the present invention can be but are not limited to Hydroxy, carboxy, ester or the like.

The drug substance content of the depot formulation (the loading) is in a range of 1% to 30%, preferred 10% to 25%, more preferred 15% to 20%. The loading is defined as the weight ratio of drug substance as free base to the total mass of the PLGA formulation.

Suitable polymers are commonly known but not limited to those commercially available as RESOMER® by Boehringer Ingelheim Pharma GmbH & Co. KG, Ingelheim, Germany, LACTEL® by Absorbable Polymers International (API), Pelham, Ala., USA, MEDISORB® by Alkermes, Inc., Cambridge, Mass., USA, PURASORB® by PURAC biochem By, Gorinchem, The Netherlands. Examples of suitable polymers are listed in Table 1.

TABLE 1

Examples of suitable polymers

| No | Product name | Polymer | Inherent viscosity [dL/g] | Producer Supplier |
|---|---|---|---|---|
| 1 | Resomer ® R 202 H | Linear Poly(D,L-lactide) free carboxylic acid end group | 0.16-0.24 [1] | Boehringer |
| 2 | Resomer ® R 202 S | Linear Poly(D,L-lactide) | 0.16-0.24 [1] | Boehringer |
| 3 | Resomer ® R 203 S | Linear Poly(D,L-lactide) | 0.25-0.35 [1] | Boehringer |
| 4 | Resomer ® RG 752 H | Linear Poly(D,L-lactide-co-glycolide) 75:25 free carboxylic acid end group | 0.14-0.22 [1] | Boehringer |
| 5 | Resomer ® RG 752 S | Linear Poly(D,L-lactide-co-glycolide) 75:25 | 0.16-0.24 [1] | Boehringer |
| 6 | Resomer ® CR RG 75:25 or Resomer ® RG Type 75:25 S/ Resomer ® RG 753 S | Linear Poly(D,L-lactide-co-glycolide) 75:25 | 0.32-0.44 [1] | Boehringer |
| 7 | Lactel ® 100D020A | Linear Poly(D,L-lactide) free carboxylic acid end group | 0.15-0.25 [2] | API/Durect |
| 8 | Lactel ® 100D040A | Linear Poly(D,L-lactide) free carboxylic acid end group | 0.26-0.54 [2] | API/Durect |
| 9 | Lactel ® 100D040 | Linear Poly(D,L-lactide) | 0.26-0.54 [2] | API/Durect |
| 10 | Lactel ® 100D065 | Linear Poly(D,L-lactide) | 0.55-0.75 [2] | API/Durect |
| 11 | Lactel ® 85DG040 | Linear Poly(D,L-lactide-co-glycolide) 85:15 | 0.26-0.54 [2] | API/Durect |
| 12 | Lactel ® 85DG065 | Linear Poly(D,L-lactide-co-glycolide) 85:15 | 0.55-0.75 [2] | API/Durect |
| 13 | Lactel ® 75DG065 | Linear Poly(D,L-lactide-co-glycolide) 75:25 | 0.55-0.75 [2] | API/Durect |
| 14 | Lactel ® 65DG065 | Linear Poly(D,L-lactide-co-glycolide) 65:35 | 0.55-0.75 [3] | API/Durect |
| 15 | Lactel ® 50DG065 | Linear Poly(D,L-lactide-co-glycolide) 50:50 | 0.55-0.75 [3] | API/Durect |
| 16 | Medisorb ® 100 DL HIGH IV | Linear Poly(D,L-lactide) | 0.66-0.80 | Alkermes |
| 17 | Medisorb ® 100 DL LOW IV | Linear Poly(D,L-lactide) | 0.50-0.65 | Alkermes |
| 18 | Medisorb ® 8515 DL HIGH IV | Linear Poly(D,L-lactide-co-glycolide) 85:15 | 0.66-0.80 | Alkermes |
| 19 | Medisorb ® 8515 DL LOW IV | Linear Poly(D,L-lactide-co-glycolide)85:15 | 0.50-0.65 | Alkermes |
| 20 | Medisorb ® 7525 DL HIGH IV | Linear Poly(D,L-lactide-co-glycolide) 75:25 | 0.66-0.80 | Alkermes |
| 21 | Medisorb ® 7525 DL LOW IV | Linear Poly(D,L-lactide-co-glycolide) 75:25 | 0.50-0.65 | Alkermes |
| 22 | Medisorb ® 6535 DL HIGH IV | Linear Poly(D,L-lactide-co-glycolide) 65:35 | 0.66-0.80 | Alkermes |
| 23 | Medisorb ® 6535 DL LOW IV | Linear Poly(D,L-lactide-co-glycolide) 65:35 | 0.50-0.65 | Alkermes |
| 24 | Medisorb ® 5050 DL HIGH IV | Linear Poly(D,L-lactide-co-glycolide) 50:50 | 0.66-0.80 | Alkermes |
| 25 | Medisorb ® 5050 DL LOW IV | Linear Poly(D,L-lactide-co-glycolide) 50:50 | 0.50-0.65 | Alkermes |

[1] IV has been determined in chloroform at a concentration of 0.1% at 25° C.
[2] IV has been determined in chloroform at a concentration of 0.5 g/dL at 30° C.
[3] IV has been determined in Hexafluoroisopropanol at a concentration of 0.5 g/dL at 30° C.

Plasma levels with low variability can be achieved over a time period of more then three month, preferentially between three and six month, only with with pharmaceutical compositions according to the present invention, not with formulations containing only one single polymer from the table above.

In addition, the pharmaceutical composition according to the present invention can be manufactured aseptically or non-aseptically and sterilized terminally by gamma irradiation. Preferred is terminal sterilization by gamma irradiation, resulting in a product with the highest sterility assurance possible.

The pharmaceutical composition according to the present invention may also contain one or more pharmaceutical excipients modulating the release behavior in an amount of 0.1% to 50%. Examples of such agents are: Poly(vinylpyrrolidone), carboxymethyl cellulose sodium (CMC-Na), dextrin, poly(ethyleneglycol), suitable surfactants such as poloxamers, also known as poly(oxyethylene-block-oxypropylene), Poly(oxyethylene)-sorbitan-fatty acid esters known and commercially available under the trade name TWEEN® (e.g. Tween 20, Tween 40, Tween 60, Tween 80, Tween 65 Tween 85, Tween 21, Tween 61, Tween 81), Sorbitan fatty acid esters e.g. of the type known and commercially available under the trade name SPAN, Lecithins, inorganic salts such as zinc carbonate, magnesium hydroxide, magnesium carbonate, or protamine, e.g. human protamine or salmon protamine, or natural or synthetic polymers bearing amine-residues such as polylysine.

The pharmaceutical composition according to the present invention can be a depot mixture or a polymer blend of different polymers in terms of compositions, molecular weight and/or polymer architectures. A polymer blend is defined herein as a solid solution or suspension of three different linear polymers in one implant or microparticle. A mixture of depots in contrast is defined herein as a mixture of two or more depots like implants or microparticles or semisolid formulations of different composition with one or more PLGAs in each depot. Preferred is a pharmaceutical composition wherein the three PLGAs are present as polymer blend.

The pharmaceutical composition according to the present invention can be in the form of implants, semisolids (gels), liquid solutions or suspensions which solidify in situ once they are injected or microparticles. Preferred are microparticles. Preparation of microparticles comprising octreotide or a pharmaceutically-acceptable salt thereof is known and for instance disclosed in U.S. Pat. No. 5,445,832 or U.S. Pat. No. 5,538,739.

The following part of the invention is focused on polymer microparticles although the descriptions are applicable for implants, semisolids and liquids as well.

The microparticles according to the present invention may have a diameter from a few submicrons to a few millimeters, e.g. from about 0.01 microns to about 2 mm, e.g. from about 0.1 microns to about 500 microns. For pharmaceutical microparticles, diameters of at most about 250 microns, e.g. 10 to 200 microns, preferably 10 to 130 microns, more preferably 10 to 90 microns.

The microparticles according to the present invention may be mixed or coated with an anti-agglomerating agent or covered by a layer of an anti-agglomerating agent, e.g. in a prefilled syringe or vial. Suitable anti-agglomerating agents include, e.g. mannitol, glucose, dextrose, sucrose, sodium chloride, or water soluble polymers such as polyvinylpyrrolidone or polyethylene glycol, e.g. with the properties described above.

For microparticles according to the present invention in dry state preferably an anti-agglomerating agent is present in an amount of about 0.1 to about 10%, preferentially about 3% to 5%, e.g. about 4% by weight of the microparticles. A preferred anti-agglomerating agent in this respect is mannitol.

Alternatively, an anti-agglomerating agent can be applied to the microparticles during their manufacturing process. For example, at the step of filtering/washing the microparticles they can be additionally rinsed with an aqueous solution of an anti-agglomerating agent. Thus, a layer of the anti-agglomerating agent is formed on the surface of the microparticles. Preferably, the anti-agglomerating agent is present in the microparticles at an amount of less than 10%, more preferred less than 2%, most preferred less than 0.5% by weight of the microparticles. A preferred anti-agglomerating agent in this respect is mannitol.

The manufacturing process for the depot formulation of the current invention is described in detail for microparticles:

The microparticles may be manufactured by several processes known in the art, e.g., coacervation or phase separation, spray drying, water-in-oil (W/O) or water-in-oil-in-water (W/O/W) or solids-in-oil-in-water (S/O/W) emulsion/suspension methods followed by solvent extraction or solvent evaporation. The emulsion/suspension method is a preferred process, which comprises the following steps:

(i) preparation of an internal organic phase comprising
  (ia) dissolving the polymer or polymers in a suitable organic solvent or solvent mixture;
    optionally dissolving/dispersing suitable additives;
  (ib) dissolving/suspending/emulsification of the drug substance in the polymer solution obtained in step (ia);
(ii) preparation of an external aqueous phase containing stabilizers and optionally but preferably buffer salts;
(iii) mixing the internal organic phase with the external aqueous phase e.g. with a device creating high shear forces, e.g. with a turbine or static mixer, to form an emulsion; and
(iv) hardening the microparticles by solvent evaporation or solvent extraction, washing the microparticles, e.g. with water, collecting and drying the microparticles, e.g. freeze-drying or drying under vacuum, and sieving the microparticles through 140 μm.

Suitable organic solvents for the polymers include e.g. ethyl acetate, acetone, THF, acetonitrile, or halogenated hydrocarbons, e.g. methylene chloride, chloroform or hexafluoroisopropanol.

Suitable examples of a stabilizer for step (iib) include Poly(vinylalcohol) (PVA), in an amount of 0.1 to 5%, Hydroxyethyl cellulose (HEC) and/or hydroxypropyl cellulose (HPC), in a total amount of 0.01 to 5%, Poly(vinyl pyrolidone), Gelatin, preferably porcine or fish gelatin.

The dry microparticles composition can be terminally sterilized by gamma irradiation (overkill sterilization), optionally in bulk or after filling in the final container resulting in the highest sterility assurance possible. Alternatively the bulk sterilized microparticles can be resuspended in a suitable vehicle and filled as a suspension into a suitable device such as double chamber syringe with subsequent freeze drying.

The pharmaceutical composition according to the present invention containing microparticles may also contain a vehicle to facilitate reconstitution.

Prior to administration, the microparticles are suspended in a suitable vehicle for injection. Preferably, said vehicle is water based containing pharmaceutical excipients such as mannitol, sodium chloride, glucose, dextrose, sucrose, or glycerins, non-ionic surfactants (e.g. poloxamers, poly(oxyethylene)-sorbitan-fatty acid esters, carboxymethyl cellulose sodium (CMC-Na), sorbitol, poly(vinylpyrrolidone), or aluminium monostearate in order to ensure isotonicity and to improve the wettability and sedimentation properties of the microparticles. The wetting and viscosity enhancing agents may be present in an amount of 0.01 to 1%; the isotonicity agents are added in a suitable amount to ensure an isotonic injectable suspension.

The invention further provides the use of a pharmaceutical composition according to the present invention for inter alias long-term maintenance therapy in acromegalic patients, and treatment of severe diarrhea and flushing associated with malignant carcinoid tumors and vasoactive intestinal peptide tumors (vipoma tumors).

The utility of the pharmaceutical compositions according to the present invention can be shown in standard clinical or animal studies.

The invention further provides a kit comprising the depot formulation in a vial, optionally equipped with a transfer set, together with a water-based vehicle in an ampoule, vial or prefilled syringe or as microparticles and vehicle separated in a double chamber syringe.

Experimental Part

The following examples are illustrative, but do not serve to limit the scope of the invention described herein. The examples are meant only to suggest a method of practicing the present invention.

EXAMPLE 1

Microparticle Preparation

An appropriate amount of the PLGA polymers is dissolved in an appropriate amount of dichloromethane to give an appropriate polymer concentration as stated in column "PLGA conc." in Table 2. An appropriate amount of drug substance is weight into a glass beaker and the polymer solution is poured over the drug substance so that the resulting microparticles have a drug load as stated in column "drug load".

E.g. for microparticles with a drug load of 20% and a polymer concentration of 20% the numbers are as the following: 3.547 g of the PLGA polymers are dissolved into 17.7 ml dichloromethane to give a 20% (wfv) polymer solution. 1.453 g of octreotide pamoate (corresponding to 1.00 g=20% octreotide free base) is weight into a glass beaker and the polymer solution is poured over the drug substance.

The suspension is homogenized with an Ultra-Turrax rotor-stator mixer with 20'000 rpm for 1 min under cooling with an ice/water mixture. This suspension is referred to as S/O suspension.

10.00 g of Polyvinylalcohol PVA 18-88, 3.62 g $KH_2PO_4$ and 15.14 g $Na_2HPO_4$ are dissolved in 2.00 L deionized water to form a 0.5% PVA 18-88 solution buffered to pH 7.4.

The S/O suspension is mixed with the 0.5% PVA18-88 solution by pumping the S/O suspension with the help of a flexible tube pump (Perpex, Viton tube) at a rate of 10 ml/min into a turbine and by pumping the aqueous solution with a gear pump (ismatec MV-ZJB with pumping head P140) at a rate of 200 ml/min into the same turbine. The two solutions are mixed in the turbine at 4'500 rpm. The homogenized S/O/W emulsion is collected into a 2 L glass beaker which is prefilled with 200 ml of the buffered PVA solution.

The S/O/W emulsion is then heated up to 52° C. in 5 h. The temperature of 52° C. is hold for further 30 min, before the batch is cooled to room temperature again. During this process escaping dichloromethane is removed by vacuum and the batch is stirred by a 4 blade-propeller-stirrer at 250 rpm.

As a result, microparticles are formed out of the S/O/W emulsion. The microparticles are collected by filtration (5 μm). They are washed 5 times with 200 ml water and dried for 36 h at 20° C. and 0.030 mbar. The dried microparticles are sieved through 140 μm and filled under nitrogen into glass vials. Prepared in that way, the microparticles are sterilized by gamma-irradiation with a dose of 30 kGy.

The particle size of the microparticles is measured by laser light diffraction. The microparticles are resuspended in white spirit using ultra sound. Table 2 gives the diameter $x_{90}$ (90% of all particles are smaller than this value) after 120 seconds of ultra sound treatment.

The assay of the microparticles is determined by HPLC after dissolving the microparticles with ultra sound in a 3:2 mixture of acetonitrile and methanol and further 1:1 dilution with a sodium acetate buffer (pH 4). The solution is cleared from residual particulate matter by centrifugation.

TABLE 2

Example 1-1: octreotide pamoate microparticles prepared by blend of three linear PLGAs.

| Ex. Batch | Drug Load (%) | PLGA conc. (%) | A | B | C | Process Info | Particle size $x_{90}$ (μm) | Assay (%) |
|---|---|---|---|---|---|---|---|---|
| 1-1 | 20 | 20 | 33 | 34 | 33 | 7/38 | 68.4 | 19.6 |

A: PLGA 65:35 ester 0.6 dL/g (%)
B: PLGA 75:25 ester 0.4 dL/g (%)
C: PLGA 85:15 ester 0.6 dL/g (%)
Process Info = Further Process Information:
7: 66 mM PBS pH 7.4
38: Turbine speed 3800 rpm instead of 4500 rpm

EXAMPLE 2

Vehicle Compositions A to G

CMC-Na, Mannitol and Pluronic F68 in an amount as given in Table 3 are dissolved in about 15 ml hot deionized water of a temperature of about 90° C. under strong stirring with a magnetic stirrer. The resulting clear solution is cooled to 20° C. and filled up with deionized water to 20.0 ml.

TABLE 3

Suitable vehicles for the microparticles (Amounts given in g)

|  | A | B | C | D | E | F | G |
|---|---|---|---|---|---|---|---|
| CMC-Na | 0 | 0 | 0.05 | 0.14 | 0.28 | 0.35 | 0.40 |
| Mannitol | 0 | 1.04 | 0.99 | 0.90 | 0.76 | 0.74 | 0.68 |
| Pluronic F68 | 0.04 | 0.04 | 0.04 | 0.04 | 0.04 | 0.04 | 0.04 |

EXAMPLE 3

Microparticle Suspension 180 mg of microparticles of example 1-1 are suspended in 1.0 ml of a vehicle of composition D (Table 3) in a 6 R vials. The suspensions are homogenized by shaking for about 30 seconds by hand. The reconstituted suspension may be injected without any issues using a 20 Gauge needle.

EXAMPLE 4

Lyophilisation of the Microparticles 180 mg of microparticles of example 1-1 are reconstituted in 1 ml of the vehicle composition F (Table 3), homogenized by stirring for 1 to 12 hours and then freeze-dried in a lyophilisator. Reconstitution of the lyophilized microparticles with 1 ml pure water (aqua ad injectabilia) resulted in fast and good wetting of the microparticles that may be injected without any issues using a 20 Gauge needle.

EXAMPLE 5

Release Profile in vivo (Rabbits)

Microparticles containing octreotide are suspended in 1 ml of a suitable aqueous vehicle and the resulting suspension is injected intramusculary (i.m.) into male New Zealand White bastard rabbits in a dose of 12 mg/kg. For each dosage form (test group) 4 animals are used. After defined time periods (indicated in the table 4) plasma samples are taken and analyzed for octreotide concentration.

TABLE 4

| | Plasma levels (dose corrected values); concentration in ng/ml | | | | | | | | | | |
|---|---|---|---|---|---|---|---|---|---|---|---|
| Ex. | Time after Administration (days) | | | | | | | | | | |
| Batch | 0.021 | 0.042 | 0.083 | 0.167 | 0.250 | 1 | 2 | 3 | 5 | 8 | 12 |
| 1-1 | 20.250 | 18.621 | 7.534 | 2.320 | 0.966 | 0.159 | 0.303 | 0.799 | 1.235 | 1.534 | 1.990 |
| Ex. | Time after Administration (days) | | | | | | | | | | |
| Batch | 19 | 27 | 33 | 40 | 47 | 54 | 61 | 68 | 75 | 82 | 89 | 96 |
| 1-1 | 1.557 | 1.404 | 0.947 | 0.903 | 1.224 | 3.204 | 2.381 | 1.887 | 2.142 | 1.511 | 0.512 | 0.284 |

The invention claimed is:

1. A sustained release pharmaceutical composition in the form of microparticles comprising as active ingredient octreotide or a pharmaceutically-acceptable salt thereof and a biocompatible polymer matrix which is a polymer blend comprising a first linear polylactide-co-glycolide polymer (PLGA) having a lactide:glycolide ratio of 85:15, a second linear PLGA having a lactide:glycolide ratio of 75:25 and a third linear PLGA having a lactide:glycolide ratio of 65:35, with each PLGA having an inherent viscosity below 0.9 dl/g in $CHCl_3$, wherein octreotide is released from the composition at a rate which maintains plasma levels of octreotide within the therapeutic range for a period of between three and six months.

2. The pharmaceutical composition according to claim 1 wherein the inherent viscosity of the PLGAs is below 0.8 dl/g in chloroform.

3. The pharmaceutical composition according to claim 1 comprising the pamoate salt of octreotide.

4. The pharmaceutical composition according to claim 1 wherein the microparticles have a diameter between 10 μm and 90 μm.

5. The pharmaceutical composition according to claim 1 wherein the microparticles are additionally mixed, covered or coated with an anti-agglomerating agent.

6. The pharmaceutical composition according to claim 5 wherein the microparticles are coated with an anti-agglomerating agent and the anti-agglomerating agent is present in an amount of less than 2% by weight of the microparticles.

7. The pharmaceutical composition according to claim 5 wherein the anti-agglomerating agent is mannitol.

8. The pharmaceutical composition according to claim 1 sterilized by gamma irradiation.

9. A method of administering octreotide or a pharmaceutically-acceptable salt thereof for long-term maintenance therapy in acromegalic patients, and treatment of severe diarrhea and flushing associated with malignant carcinoid tumors and vasoactive intestinal peptide tumors (vipoma tumors), said method comprising administering to a patient in need of octreotide or a pharmaceutically-acceptable salt thereof a pharmaceutical composition according to claim 1.

10. A process of manufacturing microparticles according to claim 1 comprising
   (i) preparation of an internal organic phase comprising
      (ia) dissolving the polymer or polymers in a suitable organic solvent or solvent mixture;
      (ib) dissolving/suspending/emulsification of the drug substance in the polymer solution obtained in step (ia);
   (iv) preparation of an external aqueous phase containing stabilizers;
   (iii) mixing the internal organic phase with the external aqueous phase to form an emulsion; and
   (iv) hardening the microparticles by solvent evaporation or solvent extraction, washing the microparticles, drying the microparticles and sieving the microparticles through 140 μm.

11. An administration kit comprising the pharmaceutical composition according to claim 1 in a vial, together with a water-based vehicle in an ampoule, vial or prefilled syringe or as microparticles and vehicle separated in a double chamber syringe.

* * * * *